United States Patent [19]
Kolter et al.

[11] Patent Number: 5,891,907
[45] Date of Patent: Apr. 6, 1999

[54] STABLE AQUEOUS SOLUBILIZATES OF CAROTENOIDS AND VITAMINS

[75] Inventors: Karl Kolter, Limburgerhof; Frank Runge, Maxdorf, both of Germany

[73] Assignee: BASF Aktiengesellschaft, Ludwigshafen, Germany

[21] Appl. No.: 813,978

[22] Filed: Mar. 10, 1997

[30] Foreign Application Priority Data

Mar. 11, 1996 [DE] Germany .................. 196 09 477.1

[51] Int. Cl.$^6$ .................. A61K 31/07; A61K 31/34; A61K 31/355; A61K 31/595

[52] U.S. Cl. .................. 514/458; 514/168; 514/474; 514/725

[58] Field of Search .................. 514/168, 458, 514/474, 725

[56] References Cited

U.S. PATENT DOCUMENTS 5,453,447  9/1995  End et al. .................. 514/763

FOREIGN PATENT DOCUMENTS

| 55 817 | 7/1982 | European Pat. Off. . |
|---|---|---|
| 479 066 | 4/1992 | European Pat. Off. . |
| 40 31 094 | 4/1992 | Germany . |
| WO 94/06310 | 3/1994 | WIPO . |
| 95/18605 | 7/1995 | WIPO . |

*Primary Examiner*—Phyllis G. Spivack
*Attorney, Agent, or Firm*—Keil & Weinkauf

[57] ABSTRACT

Stable aqueous solubilizates are disclosed suitable for parenteral administration, of carotenoids and vitamins or vitamin derivatives, in which the carotenoid and the water-insoluble vitamins are, with the aid of a nonionic emulsifier, in the form of a micellar solution, the micelles being smaller than 100 nm, wherein the solubilizates comprise, in amounts based on the solubilizate, at least one carotenoid in a concentration of from 0.1 to 10% by weight, the water-insoluble, lipophilic vitamins or vitamin derivatives in a concentration of from 0.1 to 20% by weight and the nonionic emulsifiers in a concentration of from 1 to 40% by weight, with the proviso that the content of lipophilic vitamins is at least as large as that of the carotenoid.

9 Claims, No Drawings

STABLE AQUEOUS SOLUBILIZATES OF CAROTENOIDS AND VITAMINS

The invention relates to stable aqueous solubilizates, which are suitable for parenteral administration, of carotenoids and vitamins which are prepared with the aid of nonionic emulsifiers.

Carotenoids, vitamins and trace elements have great importance in nutritional physiology. An inadequate intake into the human and animal body leads to signs of deficiency. Patients with some diseases are unable to take any food or drugs orally but require parenteral alimentation. In these cases it is also necessary to supply the abovementioned substances in this way. Furthermore, there are also cases in which patients even with oral alimentation are greatly depleted in carotenoids, vitamins and trace elements so that rapid restoration of the physiological concentrations is required. Parenteral administration is also indicated in such cases. Furthermore, preventive effects with regard to various diseases such as atherosclerosis, myocardial infarct, stroke, macular degeneration, gray cataract, Parkinson's disease and cancer are ascribed to some carotenoids, vitamins and trace elements on administration in amounts exceeding the physiological levels. In this regard it is assumed that the antioxidant, radical-scavenging properties of the substances are responsible for these effects, because it is known that oxidizing agents and free radicals lead to cellular alterations. Furthermore, these compounds which are essential for humans are thought to strengthen the immune system. Thus, on administration of vitamin E there was an increase in the T lymphocytes, especially the T helper cells.

In this connection, β-carotene and other carotenoids, tocopherol or tocopherol derivatives, ascorbic acid or ascorbic acid derivatives and selenium compounds are particularly important. A combination of these substances or some of these substances is normally referred to as antioxidant combination.

At present no formulation which is suitable for parenteral administration and which permits administration of the abovementioned carotenoids and vitamins in amounts at or above the physiological level is available.

EP 0 055 817 and DE 40 31 094 A1 disclose β-carotene solubilizates which comprise as solubilizer a nonionic surfactant with an HLB of from 12 to 16.

WO 94 06 310 A1 describes the preparation of a solubilizate of β-carotene and an emulsifier with an HLB of from 10 to 18, which is intended for use for foodstuff coloring purposes. To stabilize the β-carotene it is possible in a conventional way to add small amounts of antioxidants to the formulation.

It is an object of the present invention to propose solubilizates which comprise both β-carotene and vitamins and which are stable to precipitation and are suitable for parenteral administration. It was therefore to be expected that incorporation of other lipophilic constituents in amounts which are at least as large as the amount of β-carotene, or larger, would interfere with the micelle structure of the solubilized β-carotene in such a way that the β-carotene, which is intrinsically insoluble in water, would precipitate. Interference was likewise to be expected from larger amounts of water-soluble vitamins which are, as a rule, in the form of salts.

We have found that this object is achieved by aqueous solubilizates suitable for parenteral administration, of carotenoids and vitamins or vitamin derivatives, in which the carotenoid and the water-insoluble vitamins are, with the aid of a nonionic emulsifier, in the form of a micellar solution, the micelles being smaller than 100 nm, and being completely chemically and physically stable over a lengthy period, wherein the solubilizates comprise, in amounts based on the solubilizate, at least one carotenoid in a concentration of from 0.1 to 10% by weight, the water-insoluble, lipophilic vitamins or vitamin derivatives in a concentration of from 0.1 to 20% by weight and the nonionic emulsifiers in a concentration of from 1 to 40% by weight, with the proviso that the content of lipophilic vitamins is at least as large as that of the carotenoid.

We have furthermore found that, because of unexpected interactions between the carotenoids, the lipophilic vitamins, in particular the tocopherol or tocopherol ester, and the nonionic surfactant, the amount of nonionic surfactant in the mixture can be kept smaller than correspondence to the total in solubilizates with the individual active substances. This makes the formulation locally and systemically tolerable for humans. An additional factor is that, surprisingly, the combination of carotenoids with lipophilic vitamins in the mode of preparation makes it possible to reduce the temperature stress on the carotenoids and thus the possible decomposition. The solubilization takes place more quickly than without addition of the lipophilic vitamin.

This surprising finding of excellent stabilization is suspected to be due to the formation of mixed micelles in which interactions at the molecular level are possible.

The micelles in the solubilizates have, as a rule, average particle sizes of from 5 to 100 nm. These particle sizes are thus far smaller than the minimum requirement of 1 μm for injectable emulsions.

Suitable nonionic emulsifiers are the conventional physiologically tolerated compounds, in particular those with an HLB of from 10 to 20. Specific mention should be made of polyoxyethylene glycerol triricinoleate with 20 to 60 oxyethylene units, polyoxyethylene 12-hydroxystearate with 10 to 40 oxyethylene units, polyoxyethylene sorbitan fatty acid esters with 10 to 40 oxyethylene units and polyoxyethylene/polyoxypropylene block copolymers with the formula

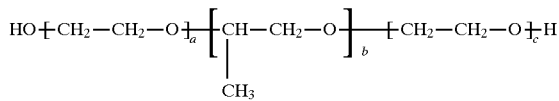

where a and c are from 10 to 130, preferably about 80, and b is from 15 to 70, preferably about 30, units.

Particularly suitable carotenoids are β-carotene, also lycopene, astaxanthin, canthaxanthin, citranaxanthin, zeaxanthin, apocarotenal and/or apocarotenoic esters, and lipophilic vitamins are tocopherol, tocopherol acetate, tocopherol succinate, retinal, retinol, retinol esters, retinoic acid, cholecalciferol and/or ergocalciferol.

The carotenoids are preferably present in amounts, based on the solubilizate, of from 0.4 to 6% by weight, the lipophilic vitamins in amounts of from 0.4 to 10% by weight and the emulsifiers in amounts of from 5 to 25% by weight.

It is also possible, of course, for the solubilizates to be further diluted with a physiologically tolerated vehicle for use in the form of ampoules, prefilled syringes, infusion solutions, drip solutions or syrups.

The aqueous phase may furthermore contain hydrophilic vitamins such as vitamin C or the vitamins of the B series, with or without minerals and trace elements, eg. selenium compounds. Finally, other pharmaceutically active substances such as N-acetylcysteine may be present in the solubilizates.

A preferred antioxidant combination comprises β-carotene, tocopherol or tocopherol esters, and ascorbic acid, with or without selenium compounds and N-acetylcysteine.

The formulations according to the invention are, as a rule, prepared by briefly heating the carotenoid with the lipophilic vitamins and the emulsifier at above 120° C., thus producing a solution, and then immediately mixing it with a solution of the hydrophilic starting materials in water or a buffer solution and thus cooling. It is also possible as an alternative to mix with water or a buffer solution and to add the hydrophilic vitamins later. Another possibility comprises briefly heating the carotenoid with the emulsifier at above 120° C. and mixing this solution with a solubilizate, separately prepared in a known manner, of the lipophilic vitamins in water or a buffer.

The preparation is preferably carried out batchwise by the process of EP 0 055 817 and, in particular, continuously by the process of EP 0 479 066. Reference is therefore expressly made hereby to these two patents and the conditions indicated therein.

After cooling, the solubilizate is, if it is to be used for parenteral purposes, sterilized by filtration, eg. through a 0.22 μm filter, and packed in ampoules, prefilled syringes, vials or infusion bottles. Sterilization by filtration can be omitted for oral administration, and the solubilizate is packed in dropping bottles or syrup bottles. In this case, it is advantageous to add sweeteners and flavorings to improve the taste during the preparation of the solubilizate or thereafter.

EXAMPLES

Example 1

23.0 g of polyoxyethylene 12-hydroxystearate with 15 oxyethylene units (Solutol® HS 15), 5.0 g of tocopherol acetate and 0.5 g of butylated hydroxytoluene were introduced into a flask through which nitrogen was passed and were heated to 180° C. Then, while stirring, 6.0 g of β-carotene were dissolved, the heating was removed and a solution of 4.9 g of sodium ascorbate and 0.1 g of ascorbic acid in 60.5 g of water for injections at about 20° C. was added to the hot mixture with turbulent mixing. This resulted in a clear, deep red, low-viscosity solubilizate which was filtered through a filter with a pore width of 0.45 μm and packed into vials with rubber stoppers.

| | |
|---|---|
| β-carotene content: | 5.8% |
| Tocopherol acetate content: | 5.1% |
| Ascorbic acid content: | 4.2% |
| Size of micelles: | 32 nm |
| pH: | 5.8 |

The formulation was still absolutely clear and had unaltered contents after storage at room temperature and 30° C. for 6 months.

Example 2

23.0 g of Solutol® HS 15 and 5.0 g of tocopherol were heated to 180° C. in a flask through which nitrogen was passed. Then, while stirring, 4.0 g of β-carotene were dissolved, the heating was removed and a solution of 4.9 g of sodium ascorbate and 0.1 g of ascorbic acid in 63.0 g of water for injections at 20° C. was added to the hot mixture. This resulted in a clear, deep red, low-viscosity solubilizate which was filtered through a filter with a pore width of 0.45 μm and packed into vials with rubber stoppers.

The formulation was still absolutely clear and had unaltered contents after storage at room temperature and 30° C. for 6 months.

| | |
|---|---|
| β-carotene content: | 3.9% |
| Tocopherol acetate content: | 5.2% |
| Ascorbic acid content: | 4.3% |
| Size of micelles: | 27 nm |
| pH: | 6.0 |

Example 3

23.0 g of Solutol® HS 15 and 10.0 g of tocopherol acetate and 0.5 g of tocopherol were heated to 180° C. in a flask through which nitrogen was passed. Then, while stirring, 6.0 g of β-carotene were dissolved, the heating was removed and a solution of 5.5 g of sodium ascorbate and 0.1 g of ascorbic acid in 54.0 g of water for injections at 20° C. was added to the hot mixture. The clear, deep red solubilizate was, after cooling to room temperature, filtered through a filter with a pore width of 0.45 μm and packed into ampoules.

| | |
|---|---|
| β-carotene content: | 5.7% |
| Tocopherol acetate content: | 10.4% |
| Ascorbic acid content: | 5.1% |
| Size of micelles: | 42 nm |
| pH: | 6.0 |

Example 4

Continuous preparation

A suspension of 40 g of β-carotene in 250 g of Solutol® HS 15, 50 g of tocopherol acetate and 10 g of butylated hydroxytoluene was introduced into a heated receiver at 70° C. This suspension was fed by means of a high-pressure pump with a throughput of 2 l/h into a heating coil immersed in an oil bath. With an internal diameter of 2 mm and a length of 6 m and with the heat transfer oil at 170° C., the residence time was set at 34 sec. This time is sufficient to dissolve the β-carotene. After the stated residence time in the heating coil, the β-carotene solution entered a T-shaped mixing chamber in which turbulent mixing took place, at an angle of 180° C., with an aqueous solution containing 6.8% sodium ascorbate, 0.2% ascorbic acid and 0.01% thimerosal from a high-pressure pump with a throughput of 4.7 l/h. Under a pressure of 25 bar, the product was discharged through a pressure control valve. A dark red micellar solution of antioxidants was obtained.

The solubilizate was filtered through a 0.45 μm filter and packed under nitrogen in vials with rubber stoppers.

| | |
|---|---|
| β-carotene content: | 3.3% |
| Tocopherol acetate content: | 4.3% |
| Ascorbic acid content: | 4.3% |
| Size of micelles: | 28 nm |
| pH: | 5.9 |

Example 5

13.0 g of Solutol® HS 15 and 0.5 g of tocopherol were introduced into a flask through which nitrogen was passed and were heated to 180° C. Then, while stirring, 4.0 g of β-carotene were dissolved, the heating was removed and 82.5 g of a separately prepared tocopherol acetate/ascorbic acid solubilizate were added to the hot mixture.

To prepare the tocopherol acetate/ascorbic acid solubilizate, 5.0 g of tocopherol acetate were mixed with 10.0 g of Solutol® HS 15 and heated to 65° C. While vigorously stirring, a solution of 4.9 g of sodium ascorbate and 0.1 g of ascorbic acid in 62.5 g of demineralized water were slowly incorporated into this mixture.

The clear, deep red antioxidant solubisate was, after cooling to room temperature, filtered through a 0.45 μm filter and packed in vials with rubber stoppers.

| | |
|---|---|
| β-carotene content: | 3.9% |
| Tocopherol acetate content: | 5.2% |
| Ascorbic acid content: | 4.3% |
| Size of micelles: | 29 nm |
| pH: | 6.1 |

Example 6

20.0 g of tocopherol acetate and 0.5 g of tocopherol were mixed with 200 g of Solutol® HS 15 in a receiver equilibrated at 80° C. Then 10.0 g of β-carotene were suspended uniformly while passing in nitrogen. This suspension was fed by means of a high-pressure pump with a throughput of 2 l/h into a heating coil immersed in an oil bath. The heating bath temperature is 170° C., and the residence time in the heating coil is about 34 sec. After leaving the heating coil, the clear red solution was collected in a flask through which nitrogen was passed. Then a separately prepared solution of 100.0 g of sodium ascorbate, 40.0 g of nicotinamide, 15.0 g of pyridoxine HCl 10.0 g of sodium riboflavin-5-phosphate× 2H$_2$O, 10.0 g of thiamine HCl and 25.0 g of dexpanthenol in a mixture of 406.0 g of 0.1 molar sodium hydroxide solution and 1164.0 g of water for injections was slowly stirred into this solution, and the formulation was cooled to room temperature and filtered through a 0.45 μm filter.

| | |
|---|---|
| β-carotene content: | 0.48% |
| Tocopherol acetate content: | 1.05% |
| Sodium ascorbate content: | 4.9% |
| Sodium riboflavin-5-phosphate × 2H$_2$O content: | 0.50% |
| Thiamine HCl content: | 0.46% |
| Nicotinamide content: | 2.10% |
| Pyridoxine HCl content: | 0.74% |
| Size of micelles: | 19 nm |
| pH: | 5.5 |

Example 7
(Comparative test)

The continuous preparation method as described in Example 4 was used to carry out the following tests:

| | | |
|---|---|---|
| Formulation A: | β-carotene | 6% |
| | Solutol ® HS 15 | 23% |
| | Water for injections ad | 100% |
| Formulation B: | β-Carotene | 6% |
| | Tocopherol | 1.2% |
| | Solutol ® HS 15 | 23% |
| | Water for injections ad | 100% |
| Formulation C: | β-Carotene | 6% |
| | Tocopherol acetate | 10% |
| | Solutol ® HS 15 | 23% |
| | Water for injections ad | 100% |

The oil bath temperature was 170° C. in each case.
Results
Formulation A: cloudy solubilizate of inadequate stability
Formulation B: cloudy solubilizate of inadequate stability
Formulation C: clear, stable solubilizate It is possible to prepare a stable solubilizate only on addition of relatively large amounts of oil-soluble vitamins, especially when the β-carotene concentrations are relatively high.

Example 8

23.0 g of Solutol® HS 15 and 5 g of tocopherol were heated to 180° C. in a flask through which nitrogen was passed. Then, while stirring, 4.0 g of β-carotene were dissolved, the heating was removed and a solution of 5.5 g of sodium ascorbate and 0.1 g of ascorbic acid in 62.4 g of water for injections at 20° C. was added to the hot mixture. The clear, deep red solubilizate was, after cooling to room temperature, filtered through a filter with a pore width of 0.45 μm and packed in vials.

| | |
|---|---|
| β-carotene content: | 3.8% |
| Tocopherol content: | 5.0% |
| Ascorbic acid content: | 5.2% |
| Size of micelles: | 27 nm |
| pH: | 6.0 |

Example 9

A suspension of 16 g of astaxanthin in 400 g of Solutol® HS 15 and 32 g of tocopherol acetate was introduced at 60° C. similarly to the continuous preparation method described in Example 4. With a throughput of 2.2 l/h, the suspension was passed through a heating coil with an internal diameter of 2 mm and a length of 12 m, which was immersed in an oil bath at about 210° C. The resulting residence time of 62 seconds was sufficient to dissolve the astaxanthin in the emulsifier. Then an aqueous solution of 1.5 g/l ascorbic acid and 37 g/l sodium ascorbate was fed in at a throughput of 5.4 l/h for turbulent mixing in the mixing chamber. The product was discharged under a pressure of 30 bar through a pressure control valve. A dark red micellar astaxanthin solution was obtained and was filtered through a 0.22 μm filter.

| | |
|---|---|
| Astaxanthin content: | 0.8% |
| Tocopherol acetate content: | 2.0% |
| Sodium ascorbate + ascorbic acid content: | 2.7% |
| Size of micelles: | 30 mm |
| pH: | 5.9 |

We claim:

1. A stable aqueous solubilizate, suitable for parenteral administration, which comprises
   a) from 0.1 to 10% by weight, based on the solubilizate, at least one carotenoid, and
   b) form 0.1 to 20% by weight, based on the solubilizate, at least one water-insoluble, lipophilic vitamin or vitamin derivative, and
   c) from 1 to 40% by weight, based on the solubilizate, a nonionic emulsifier,
wherein the carotenoid, the lipophilic vitamin or the lipophilic vitamin derivative and the nonionic emulsifier form micelles that are smaller than 100 nm, and wherein the content of the lipophilic vitamin or vitamin derivative is at least as large as the content of the carotenoid.

2. The solubilizate defined in claim 1, which comprises
   a) from 0.4 to 6% by weight the carotenoid,
   b) from 0.4 to 10% by weight the lipophilic vitamin or vitamin derivative, and
   c) from 5 to 25% by weight the nonionic emulsifier.

3. The solubilizate defined in claim 1, which further comprises at least one hydrophilic vitamin and which may further comprise minerals.

4. The solubilizate defined in claim 1, wherein the lipophilic vitamin or vitamin derivative is tocopherol or a tocopherol ester, which further comprises d) ascorbic acid,
and which may further comprise
  e) selenium compounds and
  f) N-acetylcysteine.

5. The solubilizate defined in claim 1, wherein
  a) the carotenoid is selected from the group consisting of β-carotene, lycopene, astaxanthin, canthaxanthin, citranaxantin, zeaxantin, apocarotenal and apocarotenoic esters, or a mixture of two or more of said carotenoids,
  b) the lipophilic vitamin or vitamin derivative is selected from the group consisting of tocopherol, tocopherol acetate, tocopherol succinate, retinal, retinol, retinol esters, retinoic acid, cholecalciferol and ergocalciferol, or a mixture of two or more of said vitamins or vitamin derivatives, and
  c) a nonionic emulsifier having an HLB of from 10 to 20 which is selected from the group consisting of polyoxyethylene glycerol triricinoleate, polyoxyethylene 12-hydroxystearate, polyoxyethylene sorbitan fatty acid esters and polyoxyethylene/polyoxypropylene block copolymers.

6. The solubilizate defined in claim 1, which is, directly or after dilution with a physiologically tolerated vehicle, in the form of ampoules, prefilled syringes, infusion solutions or drip solutions.

7. The stable aqueous solubilizate as defined in claim 1, wherein the solubilizate contains β-carotene, tocopherol or tocopherol acetate and ascorbic acid.

8. A process for preparing a solubilizate as defined in claim 1, which comprises briefly heating the carotenoid with the lipophilic vitamins or vitamin derivatives and the nonionic emulsifier at above 120° C. until a solution is produced and immediately mixing it turbulently with water or an aqueous solution of the hydrophilic constituents, and cooling the mixture.

9. A process for preparing a solubilizate as defined in claim 1, which comprises briefly heating only the carotenoid with the nonionic emulsifier at above 120° C. until a solution is produced and immediately mixing it turbulently with a separately prepared solubilizate of the lipophilic vitamins, and cooling the mixture.

* * * * *

UNITED STATES PATENT AND TRADEMARK OFFICE
CERTIFICATE OF CORRECTION

PATENT NO.: 5,891,907

DATED: April 6, 1999

INVENTOR(S): KOLTER et al.

It is certified that error appears in the above-identified patent and that said Letters Patent is hereby corrected as shown below:

Col. 6, claim 1, line 47, "form" should be --of from--.

Signed and Sealed this

Fifth Day of October, 1999

Attest:

Q. TODD DICKINSON

Attesting Officer

Acting Commissioner of Patents and Trademarks